United States Patent [19]

White

[11] 4,441,373

[45] Apr. 10, 1984

[54] COLLECTION TUBE FOR DRAWING SAMPLES OF BIOLOGICAL FLUIDS

[75] Inventor: Fred K. White, Miami, Fla.

[73] Assignee: American Hospital Supply Corporation, Evanston, Ill.

[21] Appl. No.: 234,869

[22] Filed: Feb. 13, 1981

Related U.S. Application Data

[63] Continuation-in-part of Ser. No. 13,244, Feb. 21, 1979, Pat. No. 4,250,893.

[51] Int. Cl.³ ............................................... B01L 2/03
[52] U.S. Cl. .................................. 73/864.02; 128/760
[58] Field of Search ......................... 73/864.02, 864.72; 128/760, 763, 765, 766, 770; 422/100

[56] References Cited

U.S. PATENT DOCUMENTS

| 3,518,804 | 7/1970 | Gerarde | 73/864.02 |
| 4,024,857 | 5/1977 | Blecher | 128/763 |
| 4,104,025 | 8/1978 | Retzer | 73/864.02 |
| 4,250,893 | 2/1981 | White | 128/767 |
| 4,314,570 | 2/1982 | Sarstedt | 128/763 |

Primary Examiner—S. Clement Swisher
Attorney, Agent, or Firm—Tilton, Fallon, Lungmus

[57] ABSTRACT

A collection tube and method for drawing samples of blood and other biological fluids, such tube having a tip construction effective in promoting the entry of such fluids into the tube and, where the tube is designed to fill by capillary attraction, in enhancing the rate and extent of such action. The fine-bore tube is transparent and is cylindrical in shape with its tip beveled to define an oval planar end surface, the long axis of the oval intersecting a plane normal to the longitudinal axis of the tube at an acute angle within the range of about 35° to 60°.

16 Claims, 3 Drawing Figures

U.S. Patent    Apr. 10, 1984    4,441,373
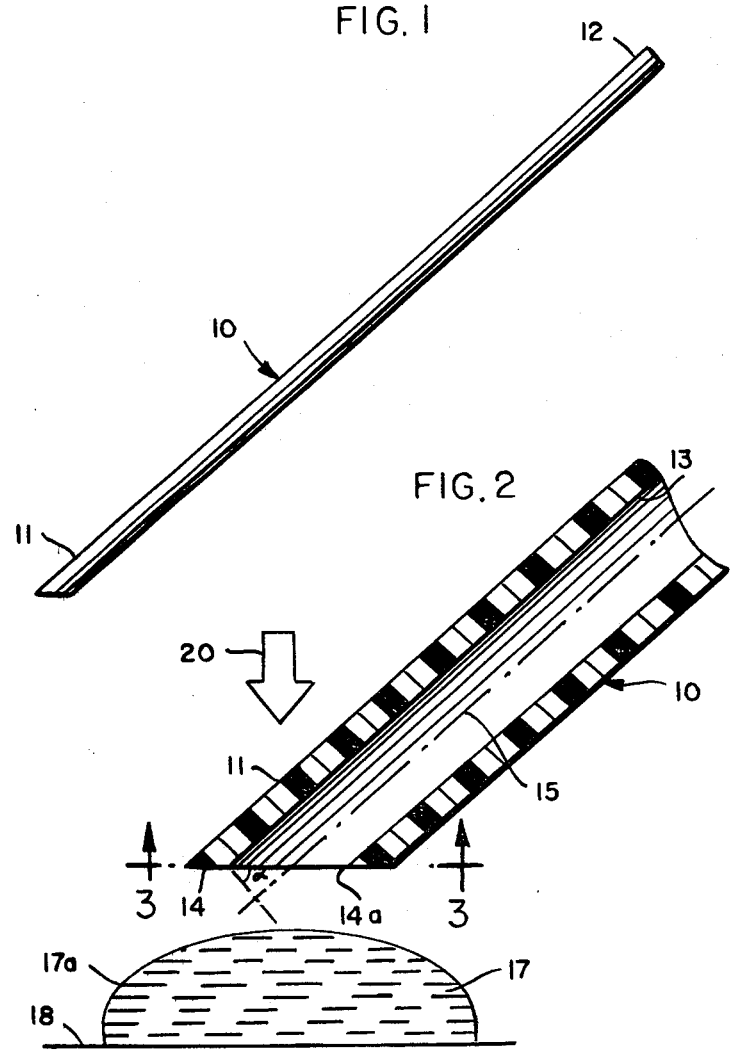
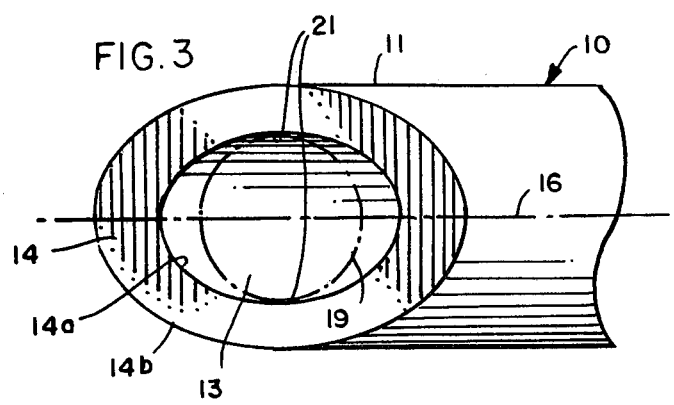

COLLECTION TUBE FOR DRAWING SAMPLES OF BIOLOGICAL FLUIDS

RELATED CASE

This application is a continuation-in-part of my copending U.S. Pat. application Ser. No. 13,244, filed Feb. 21, 1979, issuing as U.S. Pat. Ser. No. 4,250,893 on Feb. 17, 1981.

BACKGROUND AND SUMMARY

Copending U.S. Pat. application Ser. No. 13,244 discloses a sample collection device for drawing samples of blood and other fluids for clinical testing purposes. The device includes a deformable vial, a non-vented cap removably secured to the open end of the vial, and a closure member for initially sealing the collection tube and, following the collection of a sample, for closing the vial itself. The cap includes an integral collection tube extending therefrom, the tube terminating in a tip which, instead of being blunt with an end face extending at right angles to the axis of the tube, is beveled to define an oval end face sloping at an angle of approximately 45° with respect to that axis. For further details, reference may be had to such application and patent issuing therefrom, the disclosure of which is incorporated by reference herein.

A main aspect of this invention lies in the discovery that beveling the face of a tube for collecting samples of blood and other biological fluids has the important effect of reducing resistance that might exist to the entry of such fluids into the bore of the tube. The beneficial effects are particularly noticeable with fine-bore collection tubes formed of polypropylene, polyethylene, polystyrene, and other polymeric materials commonly regarded as being hydrophobic in nature. Blood and other biological fluids that would strongly resist entering the bore of such a tube if the end face were disposed at right angles, and such end face were then brought into contact with a supported drop of such a fluid, are found to enter the bore quite readily if the end face is disposed at an angle of approximately 35° to 60° measured from a plane normal to the axis of the tube. The preferred range is 40° to 55°, with the optimum being approximately 49° to 52°. Beveling the tip as so described also yields important advantages even when the tube is formed of a material generally regarded as being hydrophilic, such as glass or cellulose acetate propionate. The ease with which biological fluids may be drawn into the bore of such a tube is noticably enhanced when the tip is beveled rather than blunt, and when the oval surface of the tip is brought into contact with a body of such fluid. Furthermore, when the tube is dimensioned to be filled by capillary action, the difference in tip construction is found to yield a decrease in the fill time for such a tube.

Capillary tubes for use in collecting samples of blood and other biological fluids without the need for producing a partial vacuum or suction effect at the opposite ends of such tubes, are commonly formed of hydrophilic materials, partly because the use of other materials would make it difficult or impossible to cause liquid to enter the tubes by capillary action, and partly because such other materials exhibit insufficient attraction to such liquids to overcome the internal forces of the liquids. An important aspect of this invention lies in the discovery that if the tip of a small bore capillary tube is beveled as described, resistance to entry of biological fluids into the bore of such a tube is sufficiently diminished that such tube may be used as a standard capillary tube, being filled by capillary or gravity action, notwithstanding the fact that such tube is formed of a hydrophobic polymeric material.

Other features, objects, and advantages of the invention will become apparent from the specification and drawings.

DRAWINGS

FIG. 1 is a side elevational view of a capillary tube having a tip construction embodying the present invention.

FIG. 2 is an enlarged sectional view of the tip of the tube, such tip being shown in relation to a drop of blood resting upon a support surface.

FIG. 3 is an end view taken along line 3—3 of FIG. 2.

DETAILED DESCRIPTION

Referring to the drawings, the numeral 10 designates a blood collecting pipette in the form of a straight cylindrical tube having a tip or collecting end portion 11 and an opposite end portion 12. The bore or lumen 13 of the open-ended tube has a uniform diameter which, in the case of a capillary tube, would not exceed about 2 millimeters. The length of the tube might vary considerably in accordance with desired volumetric capacity and intended use.

A characteristic feature of collection tube 10 lies in the bevel of tip 11. End face 14, instead of extending along a plane normal to the longitudinal axis 15 of the tube, lies along a plane disposed at an oblique angle with respect to that axis. Specifically, end face 14 is oval in configuration with the long axis 16 of the oval (FIG. 3) intersecting a plane normal to the longitudinal axis 15 at an acute angle α within the range of about 35° to 60° and, preferably, 40° to 55°. The optimum range for most applications is believed to be approximately 49° to 52°, with angles in the upper part of such range believed to be more effective with tube materials of greater hydrophobicity.

The material from which collection tube 10 is formed should be rigid, transparent, and inert with respect to biological fluids. Cellulose acetate propionate has been found particularly effective, although other polymeric materials such as polystyrene, polyethylene, polypropylene, trimethyl pentene, polyethylene terephthalate, and acrylics may be used. As indicated, the tube may also be formed of glass; however, in such a case some of the benefits of the invention will not be fully realized since one of the more important advantages of this invention lies in rendering polymeric materials operative for a use for which they have not previously been regarded as well suited, largely because of the resistance to the entry of blood and other biological fluids into the bores of blunt-ended plastic tubes. Most advantageously, therefore, tube 10 is formed of a plastic material which, although relatively rigid, should not be as brittle or frangible as glass.

Referring to FIG. 3, it will be observed that the inner edge 14a of the annular end face 14 is of oval configuration, a necessary result from the facts that bore 13 is cylindrical and that planar face 14 extends at an angle within the range of 35° to 60° with respect to a plane normal to the axis of that bore. Outer edge 14b is also oval in configuration, although that is believed to be of lesser importance than the oval configuration of inner edge 14a. Outer edge 14b should be non-circular and, if oval, its long and transverse axes should ideally be superimposed or congruent with those of the oval defined by edge 14a.

The precise reasons why angling or beveling the end face of a blood collection tube markedly increases the performance of that tube may not be fully known, but it is believed that the oval configuration of end face 14, and particularly inner edge 14a, presents to the liquid droplet surface, which tries under the action of intermolecular forces to maintain a configuration of minimum area, a gradual transition from the droplet configuration to the configuration defined by the bore. This droplet surface can assume highly complex configurations as the liquid tries to satisfy the minimum area condition subject to the constraints imposed by the surrounding solid surfaces. FIG. 2 somewhat schematically illustrates a drop of blood 17 on a support surface 18. Internal molecular forces of attraction or cohesion cause that drop to minimize its surface area; if the drop were free falling rather than supported, it would tend to assume a spherical configuration. Even when supported as shown, such a drop tends to define a circular area of contact with surface 18 and to provide an exposed surface 17a of uniform convexity about a central axis perpendicular to the support surface. Consequently, when tip 11 is urged into contact with drop 17, the oval end surface 14 and its concentric edges, particularly inner edge 14a, cause a reformation of the contour of surface 17a. If the end surface 14 were at right angles to the bore of the tube instead of being beveled as shown, then contact between that face and the surface of the drop would tend to be compatible with the surface tensioning forces acting to minimize the surface of the drop; in such a case, the line of contact between the drop and the inner edge of the bore would normally be circular, as presented by phantom line 19 in FIG. 3, and such a circular line of contact would result in minimal deformation of the fluid surface within the circular opening of such a tube. In such a case, urging the blunt tip of the tube more deeply into the drop would increase hydrostatic pressure but would not appreciably alter the line of contact; hence, if a blunt-tipped collection tube were formed of a plastic material generally regarded as being hydrophobic, contact between the tip and the drop would not sufficiently disrupt the surface tensioning forces to cause the liquid to enter the bore by capillary action unless, of course, a substantial pressure head were developed. Since a drop of blood, commonly produced by pricking a finger or heel with a lancet, is of only limited volume and depth, it is difficult if not impossible to create a sufficient pressure head to overcome the surface tension and cause the fluid to enter the mouth of a blunt-tipped tube of hydrophobic material.

In contrast to the action of a blunt-ended tube, contact between the end face 14 of tube 10 and drop 17 tends to minimize the surface deformations required to transform the liquid surface from the droplet configuration to the configuration defined by the inside of the tube. If, for example, tube 10 were lowered into contact with drop 17 in the direction indicated by arrow 20, then it is believed apparent that the end face 14 would first contact the drop at two diametrically opposing points lying along the minor axis of the oval at inner edge 14a. The point contact then expands into line contact, but the line is an oval one defined by edge 14a rather than a circular one as previously described with regard to line 19. An oval line of contact along 14a, and an oval area of contact between surface 14 and liquid surface 17a, compel changes in the liquid surface that directly oppose those forces tending to minimize the surface area of the droplet. As the droplet reforms in an effort to restore itself to a condition of minimized surface area, it adopts a configuration that causes it to creep beyond edge 14a and enter the bore of the tube. Finally, once the liquid surface has entered the bore, continued flow proceeds, impelled by gravity draw and/or capillary forces.

The explanation given above for the effectiveness of the tube is theoretical and it is possible that other factors may contribute to the physical operation of the present invention, but such effectiveness of operation is readily demonstrated. Microcapillary tubes of polypropylene, polyethylene, polystyrene, polyethylene terephthalate, and other plastics generally regarded as hydrophobic have been found to operate effectively as spontaneously-filling capillary blood tubes only if their tips are beveled as described. Blood from the exposed surface of a drop readily enters the tip of such a tube and, if the tube is disposed horizontally or sloped downwardly from its tip, will quickly fill such tube even though the material from which the tube is formed is generally classified as being hydrophobic. If such a tube is formed of a material considered to be only mildly hydrophobic or hydrophilic, then filling will occur against gravity with the tube sloping upwardly from its beveled tip end.

The collection tube has been described as being formed of transparent material. The term "transparent" is used herein to mean a material having sufficient clarity to permit observation of the contents of the bore of such a tube and, therefore, such term is to be regarded as applying to materials which permit such observation even though they might be considered translucent rather than optically clear.

Tube 10 has been shown in the drawings as having a uniform outside diameter; however, it is to be understood that such tube or its tip may be tapered, as disclosed in the aforementioned copending application, and such tube may have means at its opposite end for connection to a suitable collection vessel. The structure and advantages of the invention are also illustrated by the following example.

EXAMPLE

Acrylic capillary tubes of approximately 50 microliters capacity were compared with micropipettes formed of soda-lime glass of 50 microliters capacity, marketed by American Dade Division of American Hospital Supply Corporation, Miami, Florida under the designation ACCUPETTE. Several of the acrylic tubes and, initially, all of the glass tubes, had their end surfaces at right angles to the straight uniform bores of such tubes. Other acrylic tubes were identical to the first group of acrylic tubes except that their end faces were beveled at angles within the range of 45° to 55° as described above. The testing fluid was anticoagulated blood containing one milligram per milliliter of disodium EDTA.

Each glass tube filled readily from a drop of blood carried by a support surface, using standard capillary pipetting technique. Using the same procedure with acrylic tubing having right angle tip surfaces, it was found to be extremely difficult to initiate entry of blood into the tips of the tubes, even when such tips were swirled or moved about in the blood droplets. Once entry was initiated, it was found that such acrylic tubes would fill; however, spontaneous entry of blood into the tips of such tubes, upon contact between the blunt ends thereof and the blood droplets, was not found to occur.

Spontaneous entry of blood from droplets contacted by the beveled end faces of the acrylic tubes occurred, and such tubes filled quickly and smoothly. Entry and filling were found to occur most readily with a tip angle of approximately 51°.

Certain of the glass tubes had their tips reformed to provide beveled surfaces within the range of 45° to 55° and were tested following the same procedure. Spontaneous entry occurred as before; however, a noticable reduction in fill time, as compared to glass tubes having blunt end faces, was observed.

While in the foregoing I have disclosed an embodiment of the invention in considerable detail for purposes of illustration, it will be understood by those skilled in the art that many of these details may be varied without departing from the spirit and scope of the invention.

I claim:

1. A collecting tube for drawing samples of blood and other biological fluids, comprising an open-ended tube formed of rigid transparent material and having a cylindrical bore, said tube having a beveled tip formed by a planar end surface having an oval opening defining the entrance to said bore, said end surface being sloped so that a line extending therealong and defining the long axis of said oval intersects a plane normal to the longitudinal axis of said bore at an acute angle within the range of about 35° to 60°, whereby, said oval opening promotes the spontaneous entry of a fluid sample into the bore when brought into contact therewith.

2. The tube of claim 1 in which said angle falls within the range of 40° to 55°.

3. The tube of claim 1 in which said angle falls within the range of 49° to 52°.

4. The tube of claim 1 in which said tube has hydrophobic surfaces.

5. The tube of claims 1, 2, 3, or 4 in which said tube is formed of plastic material.

6. The tube of claims 1, 2, 3, or 4, in which said cylindrical bore has a diameter no greater than about 2.0 millimeters.

7. A collecting tube for drawing samples of blood and other biological fluids, comprising a straight open-ended tube formed of rigid transparent polymeric material having a cylindrical bore of a diameter no greater than about 2.0 millimeters, said tube having a beveled tip defined by an oval planar end surface, said oval end surface having its long axis intersecting a plane normal to the longitudinal axis of said tube at an acute angle within the range of about 35° to 60°, whereby, said oval end surface and the opening therein promote the spontaneous entry of the fluid sample into the bore of the tube when said end surface is brought into contact with such sample.

8. The tube of claim 7 in which said angle falls within the range of 40° to 55°.

9. The tube of claim 7 in which said angle falls within the range of 49° to 52°.

10. The tube of claim 7 in which the surfaces thereof are hydrophobic.

11. A method for promoting the spontaneous entry of blood and other biological fluids into an open-ended cylindrically-bored collecting tube having a beveled tip providing a planar annular oval end surface, the long axis of the oval end surface extending along a line intersecting a plane normal to the axis of said bore at an acute angle within the range of about 35° to 60°, comprising the step of advancing said planar oval end surface of said tip into direct facing contact with the surface of a body of biological fluid.

12. The method of claim 11 in which said angle falls within the range of 40° to 55°.

13. The method of claim 11 in which the bore of said tube has a diameter no greater than about 2.0 millimeters and in which there is the further step of supporting said tube with said oval end surface thereof in direct facing contact with said body of biological fluid until said bore is filled by said fluid.

14. A method of promoting the spontaneous entry of blood and other biological fluids into the tip of an open-ended cylindrically-bored collecting tube formed of polymeric material, comprising the steps of beveling the tip of said tube to provide a planar annular oval end surface, the long axis of the oval end surface extending along a line intersecting a plane normal to the axis of said bore at an acute angle within the range of about 35° to 60°, and thereafter advancing said planar oval end surface into direct facing contact with the surface of a body of biological fluid.

15. The method of claim 14 in which said angle falls within the range of 40° to 55°.

16. The method of claim 15 in which the bore of said tube has a diameter no greater than about 2.0 millimeters and in which there is the further step of supporting said tube with said oval end surface thereof in direct facing contact with said body of biological fluid until said bore is filled by said fluid.

* * * * *